United States Patent
Lee et al.

(10) Patent No.: US 10,772,827 B2
(45) Date of Patent: Sep. 15, 2020

(54) COMPOSITION FOR TREATING APOPLEXY THROUGH NASAL ADMINISTRATION

(71) Applicant: INDUSTRY-UNIVERSITY COOPERATION FOUNDATION HANYANG UNIVERSITY, Seoul (KR)

(72) Inventors: Sang-Kyung Lee, Seoul (KR); Irfan Ullah, Seoul (KR); Kun Ho Chung, Seoul (KR); Jung Ju Oh, Gyeonggi-do (KR); Min Hyung Lee, Gyeonggi-do (KR); Priti Kumar, Guilford, CT (US)

(73) Assignee: INDUSTRY-UNIVERSITY COOPERATION FOUNDATION HANYANG UNIVERSITY (KR)

( * ) Notice: Subject to any disclaimer, the term of this patent is extended or adjusted under 35 U.S.C. 154(b) by 9 days.

(21) Appl. No.: 15/775,813

(22) PCT Filed: Nov. 14, 2016

(86) PCT No.: PCT/KR2016/013075
§ 371 (c)(1),
(2) Date: May 11, 2018

(87) PCT Pub. No.: WO2017/082707
PCT Pub. Date: May 18, 2017

(65) Prior Publication Data
US 2018/0325811 A1     Nov. 15, 2018

(30) Foreign Application Priority Data
Nov. 13, 2015   (KR) ........................ 10-2015-0159982

(51) Int. Cl.
| | |
|---|---|
| *A61K 9/00* | (2006.01) |
| *A61K 38/08* | (2019.01) |
| *A61P 9/10* | (2006.01) |
| *A61M 11/06* | (2006.01) |

(52) U.S. Cl.
CPC .............. *A61K 9/0043* (2013.01); *A61K 9/00* (2013.01); *A61K 38/08* (2013.01); *A61M 11/06* (2013.01); *A61P 9/10* (2018.01)

(58) Field of Classification Search
None
See application file for complete search history.

(56) References Cited

U.S. PATENT DOCUMENTS

| | | | | |
|---|---|---|---|---|
| 8,680,047 B2 * | 3/2014 | Greene | ............ | C07K 14/70578 514/4.3 |
| 2012/0245081 A1 | 9/2012 | Greene et al. | | |

FOREIGN PATENT DOCUMENTS

| | | |
|---|---|---|
| JP | 2002-540812 | 12/2002 |
| JP | 2004-290196 | 10/2004 |
| KR | 10-2010-0059862 | 6/2010 |

OTHER PUBLICATIONS

University Hospital Newark, New Jersey; The Comprehensive Stroke Center at University Hospital; http://www.uhnj.org/stroke/types.htmlm ;2013).*

(Continued)

*Primary Examiner* — James H Alstrum-Acevedo
*Assistant Examiner* — Tara L Martinez
(74) *Attorney, Agent, or Firm* — Adsero IP

(57) ABSTRACT

The present invention relates to a nasal administration composition for preventing or treating ischemic cerebrovascular disease, containing a Fas targeting peptide (FTP). When using the pharmaceutical composition or kit of the present invention, a drug can be effectively delivered to brain tissue and the ischemic cerebrovascular disease of a subject can be effectively prevented or treated.

2 Claims, 12 Drawing Sheets
Specification includes a Sequence Listing.

(56) References Cited

OTHER PUBLICATIONS

American Association of Neurological Surgeons (AANS; https://www.aans.org/Patients/Neurosurgical-Conditions-and-Treatments/Cerebrovascular-Disease; Accessed Jan. 15, 2019).*
http://www.nhlbi.nih.gov/health/health-topics/topics/stroke/treatment.html (Feb. 2011).*
Brown et al., "Intranasal Delivery of a Peptide with Antidepressant-Like Effect", Neuropsychopharmacology (2014) 39, 2131-2141.
Chelluboina et al., "Temporal Regulation of Apoptotic and Anti-apoptotic Molecules After Middle Cerebral Artery Occlusion Followed by Reperfusion", Mol Neurobiol (2014) 49:50-65.
Chen et al., "Calreticulin Binds to Fas Ligand and Inhibits Neuronal Cell apoptosis Induced by Ischemia-Reperfusion Injury", BioMed Research International, vol. 2015, Article ID 895284, 8 pages, http://dx.doi.org/10.1155/2015/895284.
Hasegawa et al., "Fas-disabling small exocyclic peptide mimetics limit apoptosis by an unexpected mechanism", PNAS, Apr. 27, 2004, vol. 101, No. 17, 6599-6604.
International Search Report for PCT/KR2016/013075, dated Feb. 20, 2017, 7 pages.
Kumar et al., "Transvascular delivery of small interfering RNA to the central nervous system", Nature, vol. 448, No. 5, Jul. 2007, 39-45.
Yin et al., "Inhibition of Apoptosis by Hyperbaric Oxygen in a Rat Focal Cerebral Ischemic Model", Journal of Cerebral Blood Flow & Metabolism (2003), 23:855-864.
Yuan, "Neuroprotective strategies targeting apoptotic and necrotic cell death for stroke", Apoptosis (2009) 14:469-477.
European Search Report for Application No. 16864633.9, dated Jun. 4, 2019, 11 pages.
Hanson, L. R. et al., "Intranasal delivery bypasses the blood-brain barrier to target therapeutic agents to the central nervous system and treat neurodegenerative disease", BMC Neuroscience 2008, 9(Suppl 3):S5 available from : http://www.biomedcentral.com/1471-2202/9/S3/S5.
Reich, Arno et al., "Fas/CD95 Regulatory Protein Faim2 is Neuroprotective after Transient Brain Ischemia", The Journal of Neuroscience, Jan. 5, 2011, 31(1):225-233.

* cited by examiner

COMPOSITION FOR TREATING APOPLEXY THROUGH NASAL ADMINISTRATION

CROSS-REFERENCE TO RELATED APPLICATION

This application claims priority to and is a 35 U.S.C. § 371 national phase application of PCT/KR2016/013075 (WO2017/082707), filed on Nov. 14, 2016 entitled "COMPOSITION FOR TREATING APOPLEXY THROUGH NASAL ADMINISTRATION", which application claims priority to and the benefit of Korean Patent Application No. 10-2015-0159982, filed Nov. 13, 2015; the disclosures of which are incorporated herein by reference in their entirety.

SEQUENCE STATEMENT

Incorporated by reference herein in its entirety is the Sequence Listing entitled "G18U10C0172P_US_ST25," created May 8, 2018, size of 1 kilobyte.

BACKGROUND

1. Field of the Invention

The present invention relates to a composition for intranasal administration to prevent or treat an ischemic cerebrovascular disease, which includes a Fas targeting peptide (FTP).

2. Discussion of Related Art

Cerebrovascular disease, often referred to as stroke, is one of the three major causes of death, along with malignant tumors and heart disease, and particularly is becoming one of the major diseases as the pace of aging of the Korean population accelerates. Stroke is a disease in which blood vessels supplying blood to the brain are clogged or burst, resulting in damage to the local part of the brain, commonly known as "apoplexy". Symptoms include hemiparalysis, sensory disorders, speech disorders, pronunciation disorders, visual impairment and visual disturbance, diplopia, headaches, dizziness, unconsciousness, vegetative states, and dementia. Stroke is divided into two types: ischemic stroke (80% to 85%) caused by no supply of blood to tissue due to complete blockage or severe narrowing of cerebral blood vessels; and hemorrhagic stroke (15% to 20%) in which the function of brain cells is impaired by bleeding. Stroke has the second highest mortality rate in Korea and the third highest mortality rate in the world. About 50% or more of stroke survivors have a variety of disorders, causing a social burden on those who need to take care of patients as well as the patients.

Ischemic stroke occurs at an overwhelmingly higher rate than hemorrhagic stroke, and various types of pathological abnormalities appear in cerebral blood vessels supplying blood to the brain, thus causing brain hemorrhage disorders in a certain region of the brain, resulting in deteriorated brain function or eventually resulting in an ischemic infarction. Ischemia refers to a state of reduced blood flow to the body organs, tissues or regions and ultimately leads to necrosis of cells and tissues, which is irreversible damage. In particular, the brain or heart is the body organ most sensitive to blood flow deficiency. For example, when ischemia occurs in a tissue due to a stroke or head injury, processes called ischemic cascades are triggered to permanently damage brain tissue. However, the surrounding tissue has a penumbra zone that can be recovered, and this area is subject to medical treatment.

In ischemic stroke, which accounts for most of the total number of strokes, there are many cases in which the prognosis of patients in the future is determined according to the clinical course of the acute phase (within 7 days) or subacute phase (within 4 weeks). In these ischemic strokes, re-opening treatment is performed to re-supply the blood stream so that the brain tissue of the ischemic penumbra, which is the physiological target of acute phase treatment, functions again. However, until now, it has been known that the prognosis of patients can be improved by re-opening using an intravenous administration method within 4.5 hours after the onset of symptoms or re-opening using an intraarterial method within 6 hours thereafter. However, a rate, at which stroke patients are found in time in the world including Korea, and can receive re-opening treatment in an appropriate emergency room, is extremely low. Since most of the acute ischemic stroke patients do not receive adequate treatment, there is therefore an urgent need for a new therapeutic method that is safe and effective in acute patients.

Meanwhile, it is known that the cascade of Fas/FasL interaction is triggered in relation to apoptosis signaling. In regard to this, conventional cyclic Fas targeting peptides have been reported as Fas mimetics (Hasegawa et al, 2004. Fas-disabling small exocyclic peptide mimetics limit apoptosis by an unexpected mechanism. Proc Natl Acad Sci USA 101:6599-6604 and US 2012-0245081, 2012 Sep. 27), and there have been attempts to treat Fas-related diseases thereby.

Throughout the present specification, many papers and patent documents are referred to and citations thereof are shown. The disclosures of the cited papers and patent documents are incorporated herein by reference in their entirety, and thus the level of the art to which the present invention pertains and the contents of the present invention will be explained more clearly.

SUMMARY OF THE INVENTION

The inventors of the present invention had intensively studied and made efforts to develop a pharmaceutical composition capable of inhibiting brain cell death by prompt transfer thereof to brain cells to prevent or treat ischemic cerebrovascular diseases. As a result, it was verified that when a Fas targeting peptide (FTP) is delivered to brain tissue via intranasal administration, brain cell death due to an ischemic cerebrovascular disease could be inhibited, and thus the present invention was completed based on the finding.

Therefore, an object of the present invention is to provide a composition for intranasal administration to prevent or treat an ischemic cerebrovascular disease.

Another object of the present invention is to provide a kit for preventing or treating an ischemic cerebrovascular disease.

Still another object of the present invention is to provide a method of preventing or treating an ischemic cerebrovascular disease.

Other objects and advantages of the present invention will become more apparent from the following detailed description of the invention, claims and drawings.

To achieve the above objects, the present invention provides a pharmaceutical composition for intranasal administration to prevent or treat an ischemic cerebrovascular disease, which includes a Fas targeting peptide (FTP) consisting of an amino acid sequence of SEQ ID NO: 1, as an active ingredient.

The present invention also provides a kit for preventing or treating an ischemic cerebrovascular disease, which includes: the pharmaceutical composition for intranasal administration; and an injection device for intranasal administration of the composition.

The present invention also provides a method of preventing or treating an ischemic cerebrovascular disease, including: intranasally administering the composition for intranasal administration to a subject in need thereof.

The features and advantages of the present invention are summarized as follows:

(a) The present invention provides a pharmaceutical composition for intranasal administration to prevent or treat an ischemic cerebrovascular disease.

(b) The present invention provides a kit for preventing or treating an ischemic cerebrovascular disease.

(c) When the pharmaceutical composition or kit of the present invention is used, it is possible to effectively deliver a drug into brain tissue.

(d) When the pharmaceutical composition or kit of the present invention is used, an ischemic cerebrovascular disease of a subject can be effectively prevented or treated.

DETAILED DESCRIPTION OF EXEMPLARY EMBODIMENTS

Figure 1A:
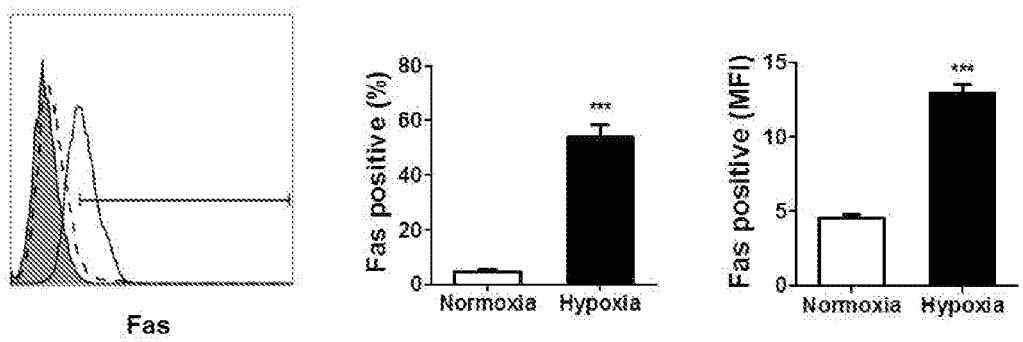
FIG. 1A illustrates the expression of Fas in hypoxic Neuro2a cells, wherein representative histograms show the expression of Fas after inducing hypoxia (left panel), cumulative data representing % Fas expression (middle panel), and MFI (right panel); the filled histograms show cells treated with isotype immunoglobulin G (isoIgG); and the dotted and solid line histograms show the expression of Fas in normoxic and hypoxic cells, respectively.

An embodiment of the present invention provides a pharmaceutical composition for intranasal administration to prevent or treat an ischemic cerebrovascular disease, which includes a Fas targeting peptide (FTP) consisting of an amino acid sequence of SEQ ID NO: 1 as an active ingredient.

The inventors of the present invention had intensively studied and made efforts to develop a pharmaceutical composition capable of inhibiting brain cell death by prompt transfer thereof to brain cells to prevent or treat ischemic cerebrovascular diseases. As a result, it was verified that when a Fas targeting peptide (FTP) was delivered to the body via intranasal administration, brain cell death due to ischemic cerebrovascular disease could be effectively inhibited.

The term "ischemic cerebrovascular disease" as used herein refers to a disease in which various types of pathological abnormalities occur in blood vessels supplying blood to the brain, resulting in an obstacle to normal cerebral blood flow, and may be interchangeably used with the term "ischemic stroke" or "cerebral infarction."

The Fas targeting peptide (FTP), which is an active ingredient of the composition for intranasal administration to prevent or treat an ischemic cerebrovascular disease, according to the present invention, has been known as a peptide sequence for inhibiting interaction between Fas and FasL, which is a ligand thereof. Fas and its specific ligand, FasL, are members of proteins belonging to the TNF receptor superfamily (TNFRSF) and the TNF ligand superfamily (TNFSF), respectively. The interaction between Fas and FasL triggers a cascade of intracellular events leading to apoptosis in Fas-expressing targets. Fas is a membrane protein expressed in various tissue cells including brain cells, and FasL is mainly expressed in lymphatic organs and immune-related tissues. It has been reported that expression of Fas is increased in ischemic brain damage (Expression of Fas and Fas Ligand After Experimental Traumatic Brain Injury in the Rat, J Cereb Blood Flow Metab. Vol. 20, No. 4, 2000).

The FTP of the present invention is a Fas peptide mimetic that inhibits Fas activity, particularly Fas-mediated signaling. However, when the composition of the present invention is administered intravenously or orally, the active ingredient does not easily pass through the blood-brain barrier (BBB), and the efficiency of delivery to the brain is significantly reduced.

Therefore, the inventors of the present invention verified that when a pharmaceutical composition including a FTP is intranasally administered, the FTP is effectively delivered to brain tissue without the problem of passing through the BBB, thereby preventing or treating brain cell death due to an ischemic cerebrovascular disease including cerebral infarction.

In one embodiment of the present invention, the composition of the present invention inhibits ischemic brain cell death. The inventors of the present invention discovered that through specific examples, the area of an ischemic site of the brain in an ischemic animal model was significantly reduced via intranasal administration of the composition of the present invention.

In one embodiment of the present invention, the ischemic brain cell death inhibition of the present invention is due to inhibition of Fas signaling through binding to Fas as a receptor for FTP. The interaction between Fas and FasL triggers the cascade of intracellular events leading to apoptosis in the Fas-expressing target, which has been described above, to increase the expression of Fas upon ischemic brain injury. The composition of the present invention, administered via a nasal route, is effectively delivered to brain tissue, and thus inhibits cascade triggering leading to cell death by Fas, the expression of which is increased by brain ischemia. The inventors of the present invention confirmed that, in the case of the presence of a drug receptor in brain tissue upon intranasal administration of the composition of the present invention, the drug is delivered, and thus a brain cell death inhibitory effect was exhibited. It was confirmed that, in the case of normal brain tissue, when the drug receptor was not expressed, the drug could not be bound thereto. In conclusion, it was confirmed that, when the composition of the present invention was intranasally administered, a receptor was required for the delivery of a drug to brain tissue, and, accordingly, it was confirmed that the drug was delivered only to damaged brain cells.

In one embodiment of the present invention, the composition of the present invention is administered via a nasal route to a subject in a sleeping, anesthetized, or unconscious state. The inventors of the present invention verified that, when the composition of the present invention was intranasally administered, i.e., when intranasally injected into a subject in a sleeping, anesthetized, or unconscious state, delivery efficiency of the composition to brain tissue was significantly increased.

The term "unconscious" as used herein refers to a state of impaired consciousness in which there are no sensory and memory actions and there is no response to external environmental stimulus. When ischemic stroke occurs, a patient is in an unconscious state, and in this case, the composition of the present invention may be intranasally administered for a period of time until a surgical operation, thereby effectively inhibiting ischemic brain cell death. In the unconscious state of a patient, it is not easy to orally administer the pharmaceutical composition, and in the case of oral administration or systemic administration via intravenous administration, drug delivery to the brain tissue is not easy, whereas, when the composition for intranasal administration of the present invention is used, the drug may be effectively delivered to the brain tissue of a subject.

The composition for intranasal administration of the present invention may be used without limitation for diseases that may be prevented or treated by inhibiting ischemic brain cell death.

In one embodiment of the present invention, the ischemic cerebrovascular disease of the present invention includes cerebral thrombosis, a cerebral embolism, or lacunar infarction. The term "cerebral thrombosis" as used herein refers to a disease that occurs when an obstruction of blood flow is generated due to artery luminal stenosis or a thrombosis caused by arteriosclerosis of a certain cerebrovascular part. The term "cerebral embolism" as used herein refers to a disease that occurs when a cerebral blood vessel is blocked due to a thrombosis generated in the heart. The term "lacunar infarction" as used herein refers to a disease that occurs by clogging of blood vessels due to a thrombosis occurring in a small penetrating artery. All of the above-described cerebrovascular diseases are involved in ischemia of cerebral tissues. The term "ischemia" as used herein refers to a condition in which the supply of blood is blocked and insufficient, resulting in necrosis at the corresponding tissue site. When the composition of the present invention is used, damage to the cerebral ischemic site may be recovered, and the above-described diseases may be treated.

Meanwhile, the FTP of the present invention is a short peptide sequence consisting of 8 amino acids set forth in the SEQ ID NO: 1, does not necessarily need to form a cyclic form as is conventionally known (U.S. Ser. No. 13/210,117, filed on Aug. 15, 2011), and may be provided in the form of a linear peptide. The term "peptide" as used herein refers to a linear molecule formed by bonding amino acid residues to each other through peptide bonds. The peptide may be prepared using a chemical synthesis method known in the art, for example, solid-phase synthesis techniques (Merrifield, J. Amer. Chem. Soc. 85:2149-54(1963); Stewart, et al., Solid Phase Peptide Synthesis, 2nd. ed., Pierce Chem. Co.: Rockford, 111(1984)) or liquid-phase synthesis techniques (U.S. Pat. No. 5,516,891). As used herein, the term "peptidomimetics" refers to molecules (e.g., peptide) that mimic the activity of a peptide, and the peptidomimetics may be prepared by designing a similar system devised to mimic the modification of a conventional peptide, peptoids (form in which a side chain is added to a nitrogen atom on a peptide backbone), or a peptide such as a β-peptide. Generally, the peptidomimetics may be designed to have increased stability or biological activity through a modified chemical structure.

According to the present invention, the peptidomimetics of the present invention may be Fas mimetics. The term "Fas mimetics" as used herein refers to peptides derived from Fas peptides and the Fas mimetics inhibit Fas activity (particularly Fas-mediated signaling).

In one embodiment of the present invention, the FTP of the present invention is a linear peptide. Linear peptide molecules are advantageous in that a synthesis process is simpler than that of a cyclic structure and no special control is required.

The pharmaceutical composition of the present invention further includes a pharmaceutically acceptable carrier, in addition to the active ingredient. The pharmaceutically acceptable carrier included in the pharmaceutical composition of the present invention, which is commonly used in formulation, but not limited to, may be lactose, dextrose, sucrose, sorbitol, mannitol, starch, acacia gum, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and mineral oil. The pharmaceutical composition may further include, in addition to the above-described components, a lubricant, a wetting agent, a sweetener, a flavoring agent, an emulsifier, a suspension, a preservative, or the like. Suitable pharmaceutically acceptable carriers and agents are described in detail in Remington's Pharmaceutical Sciences (19th ed., 1995).

The pharmaceutical composition of the present invention may be delivered to brain tissue via intranasal administration.

A suitable dose of the pharmaceutical composition of the present invention may be variously prescribed according to many factors, such as patient age, body weight, gender, pathological conditions, diet, administration time, excretion speed, and reaction sensitivity. Meanwhile, the dose of the pharmaceutical composition of the present invention is preferably 0.01 mg/kg (body weight)/day to 1,000 mg/kg (body weight)/day.

The pharmaceutical composition of the present invention may be formulated using a pharmaceutically acceptable carrier and/or an excipient by a method, which may be easily carried out by one of ordinary skill in the art to which the present invention pertains, to be prepared in a unit dose form or to be contained in a multi-dose container. Here, the formulation may be a solution in oil or an aqueous medium, a suspension, an emulsion, an extract, powder, granules, a tablet, or a capsule, and may further include a dispersing or stabilizing agent.

As used herein, the term "pharmaceutically effective amount" refers to an amount sufficient to achieve efficacy or activity of the cytokine-related peptides described above.

Another embodiment of the present invention provides a kit for preventing or treating an ischemic cerebrovascular disease, including: (a) the above-described composition for intranasal administration; and (b) an injection device for intranasal administration of the composition.

In one embodiment of the present invention, the injection device of the present invention includes a container to contain the composition for intranasal administration. The type or material of the container, which is a space capable of containing the composition of the present invention, is not particularly limited.

Specifically, for example, the kit of the present invention may include an injection device in the form of a syringe, an injection device in the form of a sprayer, or an injection device in the form of a tube, through which the drug may be intranasally injected, but the present invention is not necessarily limited thereto. When a syringe-type injection device is included, a discharge portion corresponding to a syringe needle may be inserted into the nasal cavity of a subject, and then a discharge pressure applying part corresponding to a piston of the syringe may be operated to administer the composition of the present invention in a liquid phase to the nasal cavity. At this time, the form of the injection device is not limited to the conventional syringe type. In the case of an injection device in the form of a sprayer, as in the case of using a syringe-type injection device, a discharge portion is placed in a nostril, which is the entrance to the nasal cavity or in the nasal cavity, and then a spraying pressure is applied thereto so that the composition of the present invention may be intranasally administered in a spray form. When a tube-shaped injection device is included, as described above, a discharge portion may be inserted into the nasal cavity of a subject, and then a pressure may be applied to the tube, and in such a manner, the composition of the present invention may be intranasally injected in a liquid phase.

The above-described types of the injection device are only for illustrative purposes, and any injection device may be used without particular limitation so long as it is capable of intranasally injecting the composition of the present invention.

The present invention also provides a method of preventing or treating an ischemic cerebrovascular disease, including intranasally administering the above-described composition for intranasal administration to a subject in need thereof.

The composition for intranasal administration may be contained in an injection device including a container capable of containing the composition to be administered to the nasal cavity.

The intranasal administration may be performed while a subject is in a sleeping, anesthetized, or unconscious state.

The ischemic cerebrovascular disease may be cerebral thrombosis, a cerebral embolism, or lacunar infarction.

The subject may be, but is not limited to, mammals such as dogs, cats, rats, mice, and humans.

Hereinafter, the present invention will be described in further detail with reference to the following examples. These examples are provided only for the purpose of further illustrating the present invention, and it will be obvious to those of ordinary skill in the art that these examples are not intended to limit the scope of the present invention according to the essence of the present invention.

Example 1: Treatment of Ischemic Cerebrovascular Disease Through Intranasal Administration of Fas Targeting Peptide (Experimental Method)

1. Peptides

Peptides used in the examples of the present invention were constructed at Peptron. The sequence of a Fas targeting peptide was SEQ ID NO: 1 YCDEHFCY, and the sequence of a scrambled peptide was SEQ ID NO. 2 YCNSTVCY.

2. In Vitro Ischemia Model

Mouse neuroblastoma (Neuro2a, N2a) cells were obtained from ATCC and cultured in Dulbecco's Modified Eagle's Medium (DMEM) containing 10% fetal bovine serum (FBS), penicillin (100 IU/ml), and streptomycin (100 μg/ml). To duplicate an ischemia/reperfusion environment in vitro, the Neuro2a cells were cultured in a 6-well plate and maintained under a hypoxic condition (94% $N_2$, 5% $CO_2$, and 1% $O_2$) in an oxygen glucose deprivation (OGD) medium (Life Technologies) for 24 hours. Subsequently, the cells were re-oxygenated in DMEM supplemented with 10% FBS (5% $CO_2$, 20% $O_2$, 37° C.) for 24 hours.

3. In Vitro Fas Expression and FTP Binding

To identify co-localization of a FTP and a Fas receptor, Neuro2a cells were seeded on a cover slip and maintained under a hypoxic condition in an OGD medium for 24 hours. After incubating for 24 hours, the cells were treated with PBS containing 1% BSA and 0.05% Tween 20 and blocked at 37° C. for 2 hours, followed by staining with an anti-Fas antibody (Abcam) and an Alexa647-conjugated FTP at 4° C. for 2 hours. After incubating for 2 hours, the cells were washed three times with PBS containing 0.05% Tween 20, and stained with a secondary antibody (Abcam) at 4° C. for 2 hours under a dark condition. Nuclei of the cells were counterstained with Hoechst 33342 and fixed with an aqueous mounting solution (Abcam). Fluorescence signals in the cells were obtained using a TSP-SP5 confocal microscope (Leika, Germany).

4. Inhibition of In Vitro Fas-Mediated Apoptosis

To examine an inhibitory effect of a FTP, hypoxia-induced Neuro2a cells were treated with 1,000 μM of a FTP. After incubating for 24 hours, the cells were stained using a PE Annexin V apoptosis detection kit (BD Pharmingen™) according to the manufacturer's instructions.

5. Experimental Animals and Study Design

For the experiments, Sprague-Dawley (SD) rats weighting 280 g to 320 g were purchased from Orient Bio and placed in a pathogenic free laboratory. All experiments were performed in accordance with compliance guidelines and protocols approved by the Institutional Animal Care and Use Committee of Hanyang University. Animals were housed in 12 hour light/dark cycles at controlled temperature and humidity with free access to water and food. To exclude any gender related difference to adopt brain damage, only male SD rates were used. 2 weeks after being exposed to a new environment, the animals were divided into four groups. A first group of animals were not subjected to surgery and used as a control. For the remaining groups of animals, middle artery cerebral occlusion (MCAO) was induced. 1 hour after surgery, animals in which ischemia was not induced and animals that did not show any difference in behavior were excluded from the experiment, and the remaining animals were randomly divided into groups for treatment. At least four individuals were included in each group.

6. Middle Cerebral Artery Occlusion (MCAO) Experimental Model

To induce a cerebral ischemic condition, animals were treated according to a conventionally known MCAO procedure[1]. Briefly, animals were anesthetized with 5% isoflurane. Thereafter, the anesthetized state was maintained at 2% isoflurane under the same gas conditions during the surgery. A heating pad was used to maintain the body temperature between 37±5° C. during surgery. The neck of each rat was shaved for about a 2.0 cm midline skin incision. The external carotid artery (ECA) was exposed while cautiously preserving the vagus nerve, and then ligated with silk thread. The same was done for the common carotid artery (CCA) and the internal carotid artery (ICA), but the ligating process was not performed. The middle cerebral artery (MCA) was occluded by inserting a prepared 3.5 cm suture (4-0 nylon suture) through the ECA into the ICA and the suture thread was pushed into the MCA. Thereafter, the CCA was completely occluded using a clip. After 1 hour of occlusion, the suture was pulled to cause reperfusion.

7. Intranasal Inoculation of FTP

Intranasal administration of peptides was performed using a pressurized olfactory delivery (POD) device (Impel Neuropharma). Briefly, rats were kept in an isoflurane chamber containing 5% isoflurane for 3 minutes. After the animals were deeply anesthetized, the rats were placed in a supine position for drug injection. A POD tip (Impel Neuropharma) was carefully inserted into a nostril, and then a prefilled 25 μl catheter tube was slowly inserted appropriately 2 cm into the nostril. Thereafter, a peptide solution (PBS) (15 μl of PBS and 500 nM peptide) was slowly injected thereinto. A total of 700 μg of the FTP peptide was intranasally injected 12 hours after MCAO. After intranasal administration, the rats were maintained in the supine position for 5 minutes before they kept back to their designated cage.

8. Bio-Distribution of Alex$^{488}$-Labeled FTP

A total of 500 μg of FTP was conjugated with Alexa-488 according to the manufacturer's guidelines (Molecular probes, Life Technologies). The Alexa$^{488}$ conjugated short peptide was intranasally injected with a final volume of 25 μl into each nostril using a POD device 12 hours after MCAO. After a predetermined period of time, the animals were sacrificed and tissues were excised therefrom. The tissues were washed with cold PBS and surface meninges were removed to avoid auto-fluorescence. The brains were observed to detect fluorescence signals using Image Station (Kodak). To evaluate a delivery rate (%), a single cell suspension was prepared from brain slices using a 40 μm cell strainer (BD Falcon). The FTP-Alexa$^{488}$-bound cells were acquired through flow cytometry (BD FACS Calibur™) and analyzed using Flowjo software.

9. TTC Staining and Measurement of Infract Volume

After a predetermined period of treatment, the brain was immediately removed. The expected area of damage in the brain was sliced into 3 slices (2 mm thick) including a brain matrix and then incubated in 2% 2,3,5-triphenyltetrazolium chloride (TTC, Sigma) at 37° C. for 10 minutes. The brain slices were then fixed in 4% paraformaldehyde and kept at 4° C. for 24 hours until imaging and photographing. The infarct volume was measured using Image J developed by the U.S. National Institute of Health (NIH) and calculated as commonly known.

10. Western Blotting

Neuro2a cells were lysed using a RIPA lysis buffer in the presence of 1 μM phenylmethylsulfonyl fluoride (PMSF) as a protease inhibitor. A total of 50 μg of protein was loaded in a 12% SDS-PAGE gel and transferred onto a nitrocellulose transfer membrane (Whatman). Blots were blocked with 5% skim milk in TBST at room temperature for 2 hours and incubated at 4° C. with primary antibodies (Abcam). After a predetermined period of time, the blots were washed with TBST and incubated for 2 hours with secondary polyclonal antibodies coupled with HRP. After washing the blots three times with TBST, the blots were developed using an ECL western blotting substrate (Promega).

11. Histology and Immunohistochemistry

Paraffin-embedded brain sections were de-paraffinized, rehydrated and then subjected to H&E staining according to standard protocols. The H&E stained sections were covered with cover slips and roughly analyzed using an optical microscope.

For immunohistochemistry, sections were heat-inactivated with a pre-warmed antigen retrieval buffer (10 mM sodium citrate, 0.05% Tween-20(w/v), pH 6.0) at 95° C. for 25 minutes and cooled at room temperature. Next, the sections were blocked with TBST containing 1% BSA and 10% goat serum at 37° C. for 1 hour and incubated with Fas primary antibodies (Abcam) overnight at 4° C. After a specified time, the sections were washed with TBST and treated with HRP-conjugated secondary polyclonal antibodies for 2 hours. After washing the sections five times with TBST, the sections were developed using a DAB substrate (GE Healthcare).

12. TUNEL Analysis

A extent of apoptosis in de-paraffinized and rehydrated brain sections was analyzed through TUNEL analysis using an In Situ Cell Death Detection Kit (Roche, Germany) according to the manufacturer's instructions.

13. Neurological Evaluation

The neurological deficits of each group of rats with or without peptide treatment were evaluated using a commonly known method[2]. Briefly, the rats that did not show visible neurological deficits were graded as 0. If the animals showed forelimb flexion, they were awarded grade 1. Next, the animals were placed on absorbent pads and tails thereof were pulled to examine their grips power. Grade 2 was given to only those animals that showed weak grips power. The rats were placed in a sufficiently wide space and allowed to move freely. Grade 3 was given for the case in which rats moved in a circle towards the paralyzed side when tails thereof were pulled. Grade 4 was given for the case in which rats spontaneously moved in a circle under a free environment.

14. Survival Curve

The survival rate of each group of animals was evaluated using a previously described method[3].

15. Statistical Analysis

Data of the present invention was statistically analyzed by a Mann-Whitney test for analyzing a difference between mean values of two groups and one-way ANOVA for analyzing a difference between mean values of two or more groups by using Graphpad Prism 5 software. $P<0.05$ was considered statistically significant.

(Experimental Results)

1. Blocking of Fas Restores Hypoxia-Induced Apoptosis In Vitro

To examine the effect of Fas-blockade in an in vitro ischemic model, Neuro2a cells were cultured in an oxygen glucose deprivation (OGD) medium for 24 hour under hypoxic conditions to induce Fas expression. The hypoxic conditions induced at least 50% Fas-expressing hypoxic cells (see FIG. 1A).

Figure 1B:
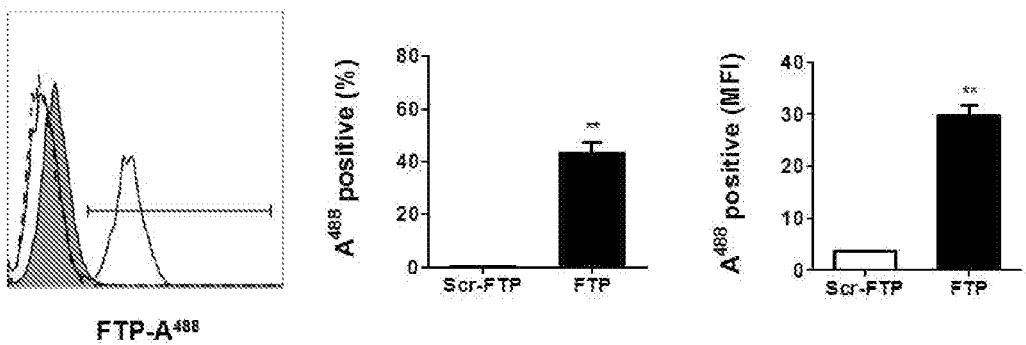
FIG. 1B illustrates binding of a FTP to hypoxic Neuro2a cells, wherein the representative histograms show binding of a FTP in Fas-expressing Neuro2a cells (left panel), cumulative data representing % Fas expression (middle panel), and MFI (right panel) obtained from Scr-FTP or FTP conjugated with Alexa$^{488}$; the filled histograms show hypoxic cells treated with isoIgG; and the dotted and solid line histograms show binding of Scr-FTP and FTP, respectively to hypoxic cells.
Figure 1C:
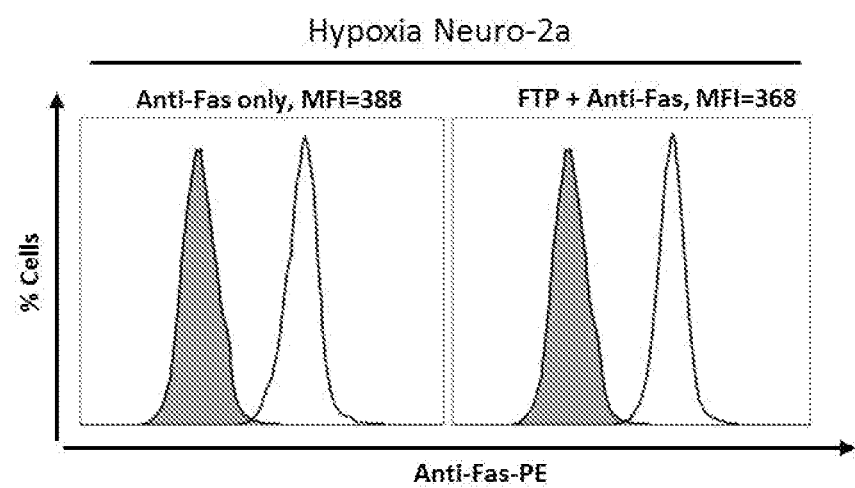
FIG. 1C illustrates the results of a competition assay of a Fas antibody and a FTP, wherein the representative histograms show binding of a Fas antibody to hypoxic cells after treatment with a FTP; data is expressed as mean±SD of three replicated experiments; P<0.01, *P<0.001; Normoxia represents cells maintained under normal culture conditions, and Hypoxia represents cells cultured in an OGD medium for 24 hours, followed by re-oxygenation in a serum-containing DMEM medium for 24 hours; and FTP: Fas targeting peptide, Scr-FTP: scrambled peptide.
Figure 2A:
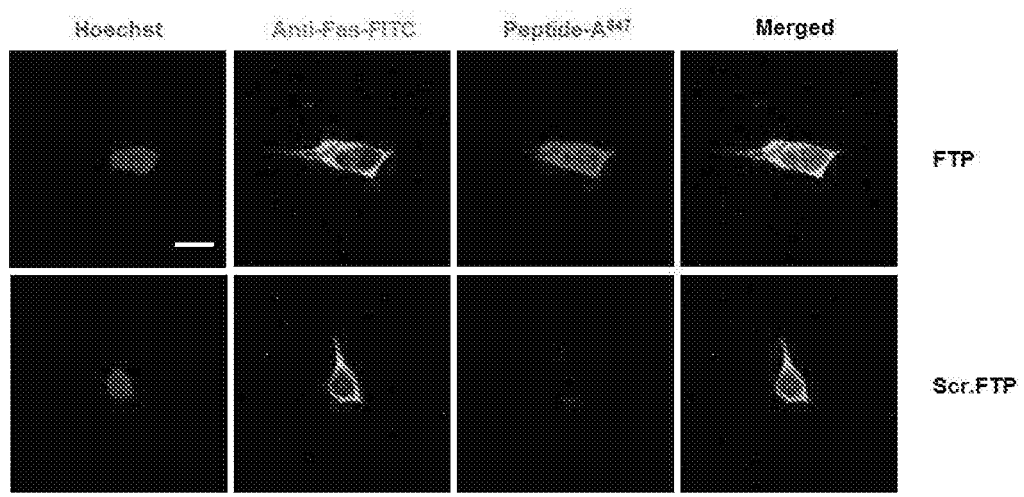
FIG. 2A illustrates that a FTP was specifically bound to Fas-expressing hypoxic Neuro2a cells and illustrates representative confocal microscopic images showing Hoechst-stained nuclei (blue), Fas expression (green), a FTP bound to Fas-expressing cells (red), and co-localization of Fas and a FTP (yellow).

Subsequently, the hypoxic cells were treated with a fluorescence-labeled Fas-targeting peptide (FTP) or a scrambled-FTP (ScrFTP) as a control peptide. A FTP was only bound to the Fas-expressing hypoxic cells and die not bind to normal cells, and the control peptide ScrFTP did not bind to the hypoxic cells (see FIG. 1B). Confocal microscopic images show that FTP was strongly engaged to the Fas-expressing cells (see FIG. 2A). As a result of competitive assay between the FTP and α-Fas antibody, the FTP and the α-Fas antibody were bound to different regions of a Fas molecule (see FIG. 1C).

Figure 2B:
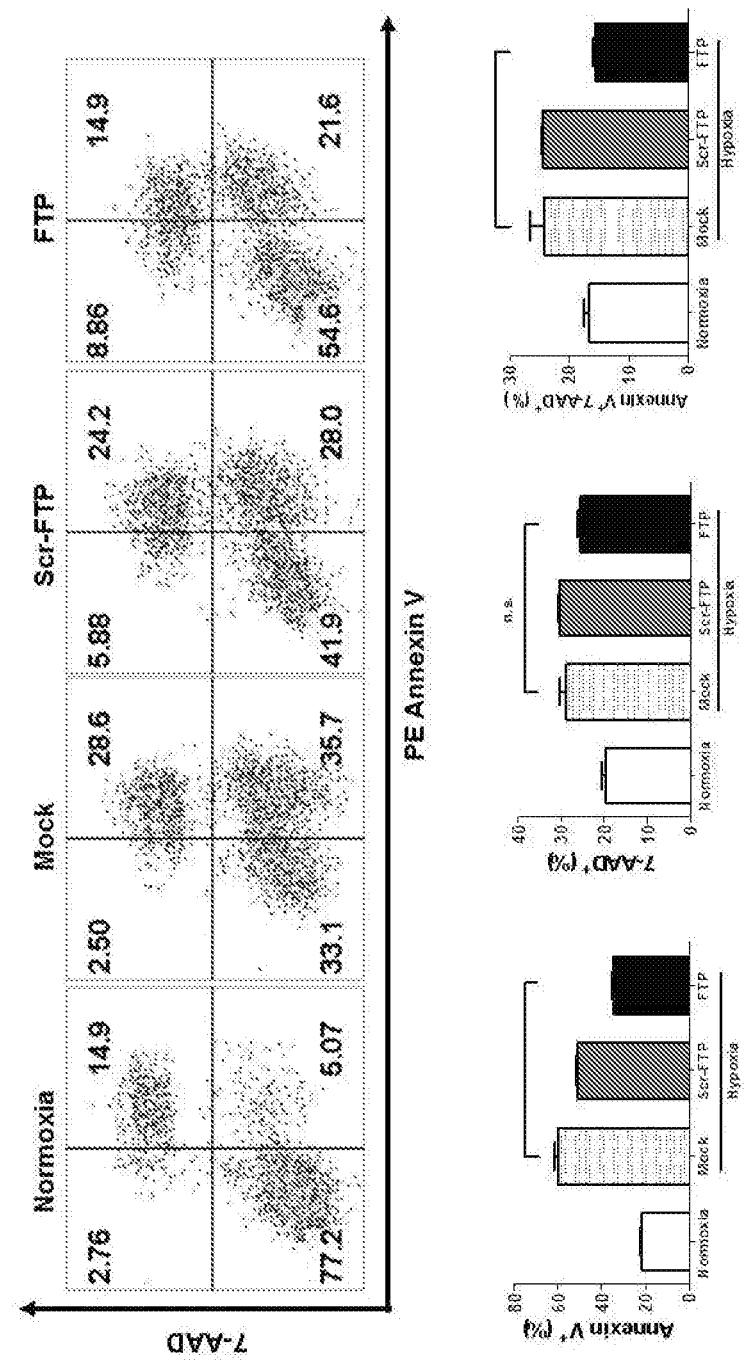
FIG. 2B illustrates flow cytometry analysis results of apoptosis in Neuro2a cells, and representative dot plots (upper panel) and cumulative data (lower panel) showing annexin V positive cells, 7-AAD positive cells, and double positive cells for both annexin V and 7-AAD (%).

An increase in Fas expression under hypoxic conditions leads to increased apoptosis in an in vitro ischemic model. Thus, annexin V- and 7-AAD positive cells were significantly increased by ~60% and ~30%, respectively, in hypoxic cells compared to cells maintained in a normoxic environment (see FIG. 2B, upper panel). However, hypoxic cells treated with a FTP prior to the removal of oxygen protected Neuro2a cells from hypoxia-induced cell death. The FTP treatment significantly decreased both annexin V positive cells and annexin V/7-ADD positive cells by ~50% (see FIG. 2B, lower panel). However, after the FTP treatment, any significant decrease was not observed in 7-AAD positive cells.

Figure 2C:
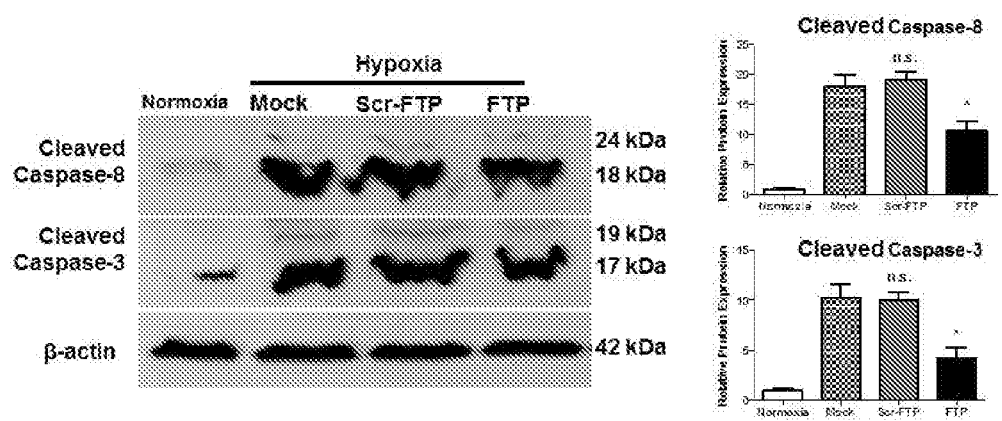
FIG. 2C illustrates representative western blotting results (left panel) showing cleaved caspase-8 and caspase-3 proteins and a bar graph (right panel) showing relative levels of proteins normalized for β-actin using ImageJ software (right panel), wherein data is expressed as mean±SD; P<0.01, *P<0.001, n.s.—not significant; Normoxia represents cells maintained under normal culture conditions, and Hypoxia represents cells maintained in an OGD medium for 24 hours, followed by re-oxygenation in serum-containing DMEM medium for 24 hours; In all cases, cumulative data were obtained from three replicated experiments; and FTP-A$^{488}$: Alexa$^{488}$-labeled FTP, ScrFTP: scrambled-FTP peptide, OGD: oxygen glucose deprivation.
Figure 3:
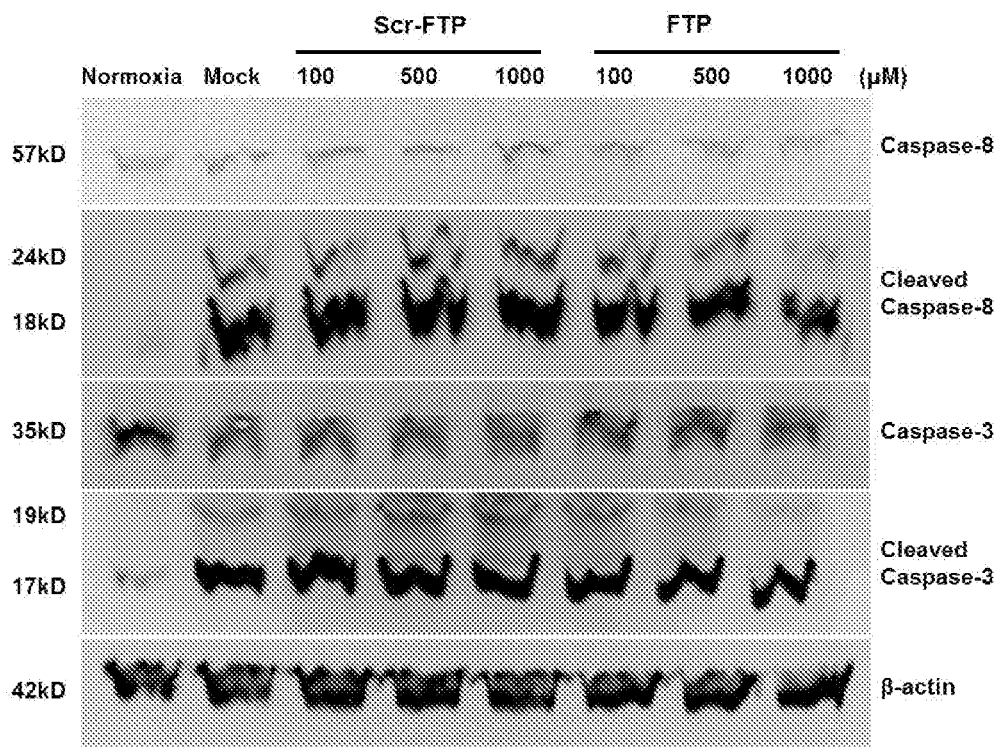
FIG. 3 illustrates representative western blotting images showing full length, cleaved caspase-8, and cleaved caspase-3, wherein Normoxia represents cells maintained under normal culture conditions, and Hypoxia represents cells maintained in an OGD medium for 24 hours, followed by re-oxygenation in serum-containing DMEM medium for 24 hours; and FTP: Fas targeting peptide, Scr-FTP: scrambled peptide.

Since the FTP blocks only a Fas-mediated extrinsic apoptosis pathway, activated cascade molecules related to Fas-mediated apoptosis were evaluated. Increased Fas triggers extrinsic apoptotic signaling molecules such as cleaved caspase-8, caspase-3, and the like. To examine whether FTP treatment could block the activation of caspase-8 and caspase-3 related to the Fas-mediated extrinsic apoptosis pathway in hypoxic cells, the activation of caspase-8 and caspase-3 was evaluated by treating hypoxic cells with a FTP according to concentration. ScrFTP-treated cells did not decrease cleaved caspase 8, whereas the FTP treatment significantly reduced the regulation of caspase-8 and caspase-3 (see FIG. 2C). The FTP treatment decreased cleaved caspase-8 and caspase-3 by ~50% and 40%, respectively. The expression of both activated cleaved caspase-8 and activated caspase-3 was decreased in a dose-dependent manner without a dramatic change at a full-length enzyme level (see FIG. 3).

Overall, these results suggest that the FTP is effectively bound to Fas-expressing cells and therapeutically rescues cells from Fas-mediated apoptosis.

Figure 4A:
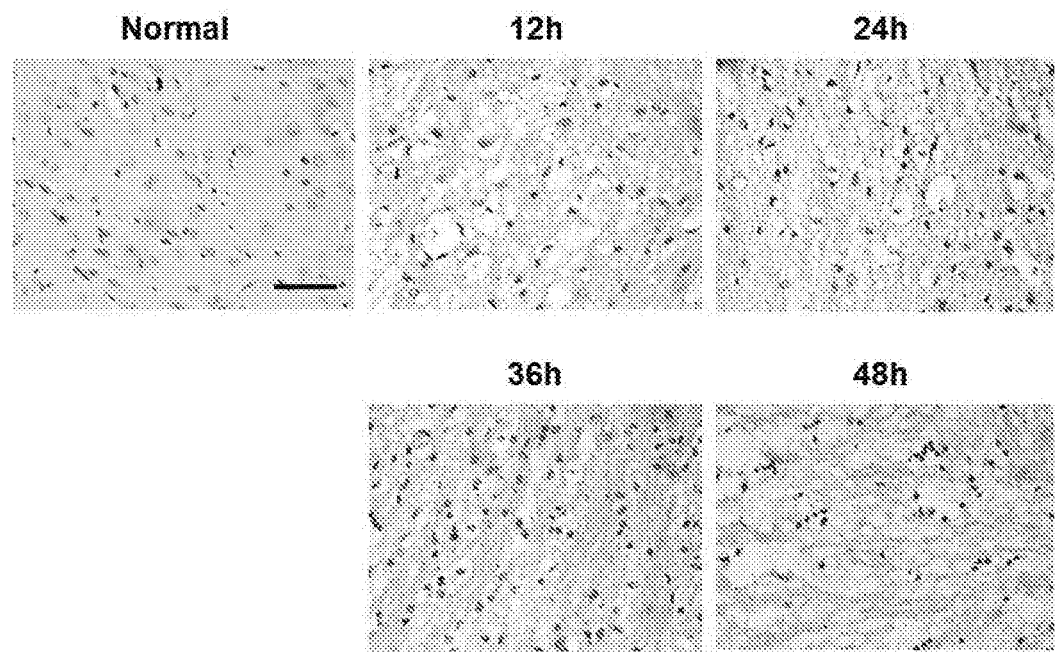
FIG. 4A illustrates images showing the expression of Fas in the brain exposed to middle cerebral artery occlusion (MCAO) surgery, wherein the representative microscopic images show Fas expression in normal and ischemic cores of the brain at indicated hour's post-reperfusion; and the scale bar represents 100× and 400× in the main drawing and the inset, respectively.
Figure 4B:
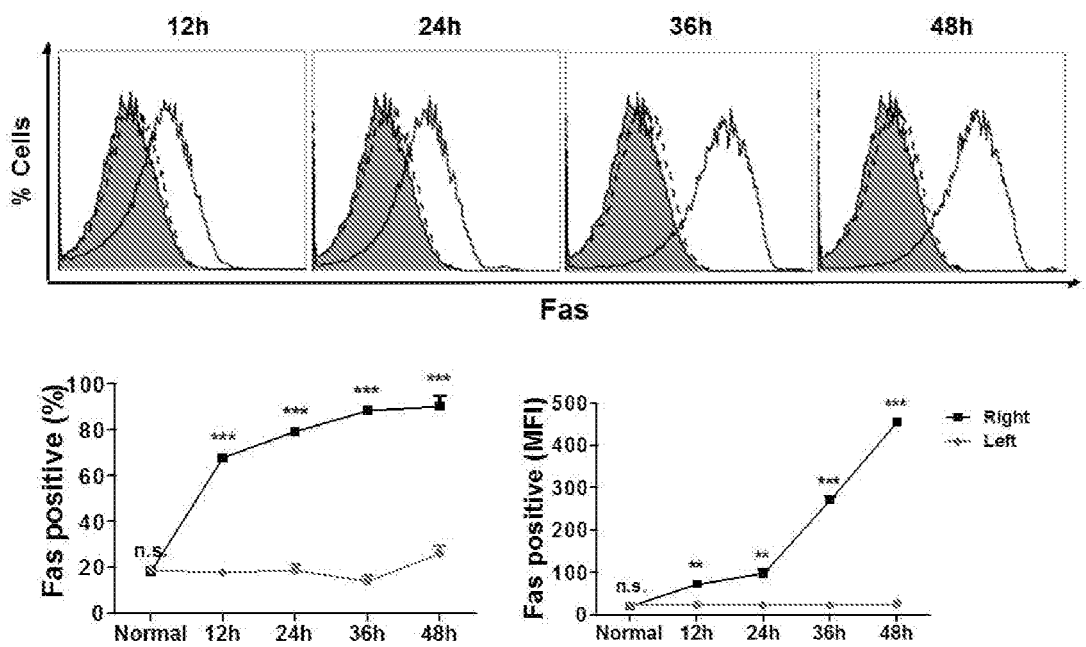
FIG. 4B illustrates fluorescence-activated cell sorting (FACS) measurement results of Fas expression in a single cell suspension prepared from left and right hemispheres of a normal rat brain and a MCAO rat brain (n=3) at indicated hour's post-reperfusion, wherein the representative histograms are illustrated at an upper panel, and show cumulative data representing % Fas expression (lower left panel) and mean fluorescent intensity (MFI) (lower right panel); and the filled histograms show a normal rat brain, whereas the dotted and solid line histograms respectively show contralateral and ipsilateral cores of the brain of rats subjected to MCAO surgery.

2. Intranasal Administration of Fas Targeting Peptides Alleviates Fas-Mediated Apoptosis Cerebral ischemia increases the expression of Fas in the brain several hours after MCAO, but the expression of Fas is insignificant under normal conditions. In right hemisphere peaking (see FIG. 4A) 48 hours after reperfusion by immunohistochemistry of brain tissue during right MCAO, which induces ischemia in the right side of the brain, or in flow cytometry analysis of a single cell suspension of brain cells (see FIG. 4B), it was confirmed that the expression of Fas was selectively increased in a time-dependent manner. 12 hours, 24 hours, and 48 hours after MCAO, 20%, 60%, and 70%, respectively, of Fas-expressing cells were found, and mean fluorescence intensities (MFIs) were increased 4-fold, 12-fold, and 18-fold at each time point. Compared to the right hemisphere, the expression level of Fas was observed to be insignificant in the left hemisphere at each time point except for 48 hours after MCAO, which suggests that the right hemisphere is much more sensitive to apoptosis after left MCAO (see FIG. 4B, lower panel).

Figure 4C:
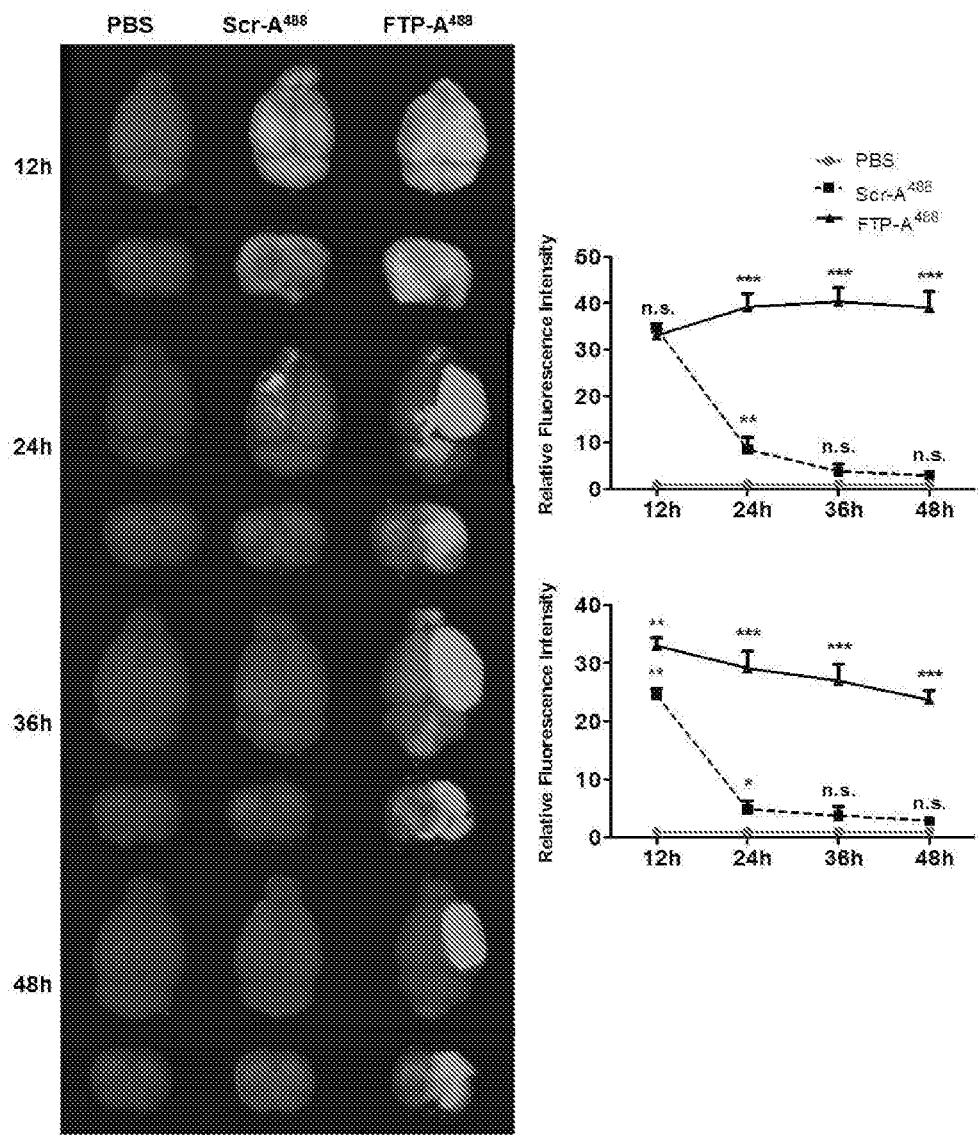
FIG. 4C illustrates the bio-distribution of an intranasally inoculated FTP in a MCAO model (three individuals), wherein the brain (top view and coronal view) was examined for the presence of Alexa$^{488}$-labeled FTP (FTP-A$^{488}$) at indicated hour's post-inoculation; PBS, a scrambled peptide labeled with Alexa$^{488}$ (Scr-A$^{488}$) or a FTP labeled with Alexa$^{488}$ (FTP-A$^{488}$) is shown; and in representative images (left panel) and a top view (right upper panel) and a coronal view (right lower panel), cumulative data representing relative fluorescence intensity were measured at an arbitrary pixel value for each isolated organ from indicated test cohort±standard error.
Figure 4D:
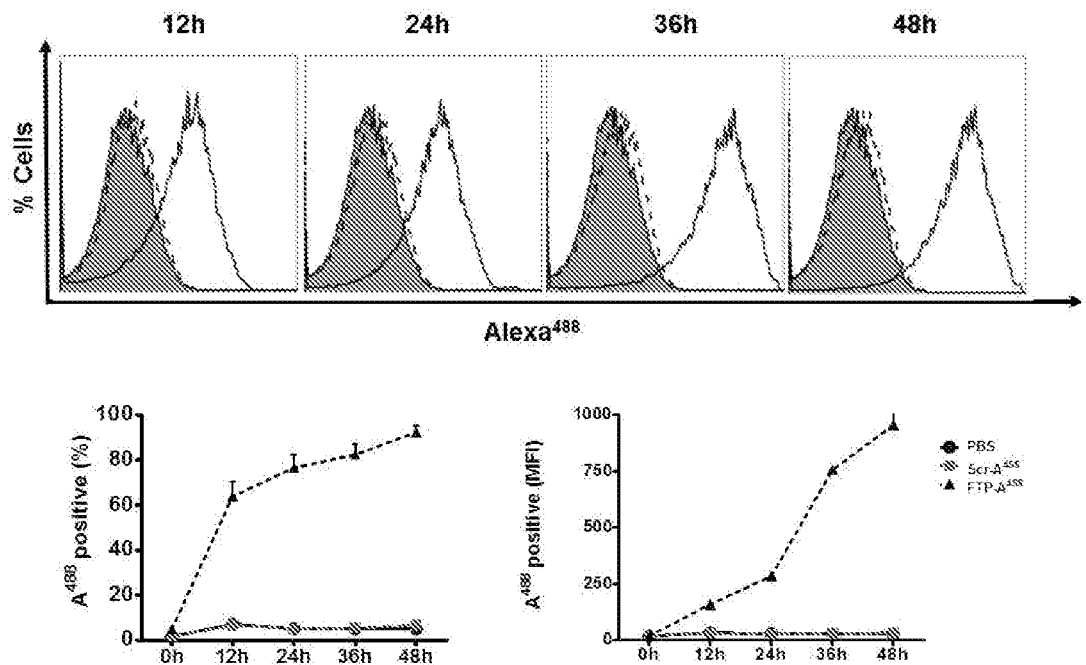
FIG. 4D illustrates flow cytometry analysis results of brain cells, wherein a single cell suspension derived from an ipsilateral core of each represented group (three per group) was prepared at indicated hour's post-inoculation; PBS, Scr-A$^{488}$, or FTP-A$^{488}$ derived from MCAO rats is shown; and representative histograms (upper panel) and an ipsilateral region (lower left panel) show cumulative data representing % FTP-Alexa$^{488}$ positive cells and MFI is shown at a lower right panel, the filled histograms correspond to PBS-treated rats, and the dotted and open histograms respectively show Scr-FTP-treated rats and FTP-treated rats.
Figure 5:
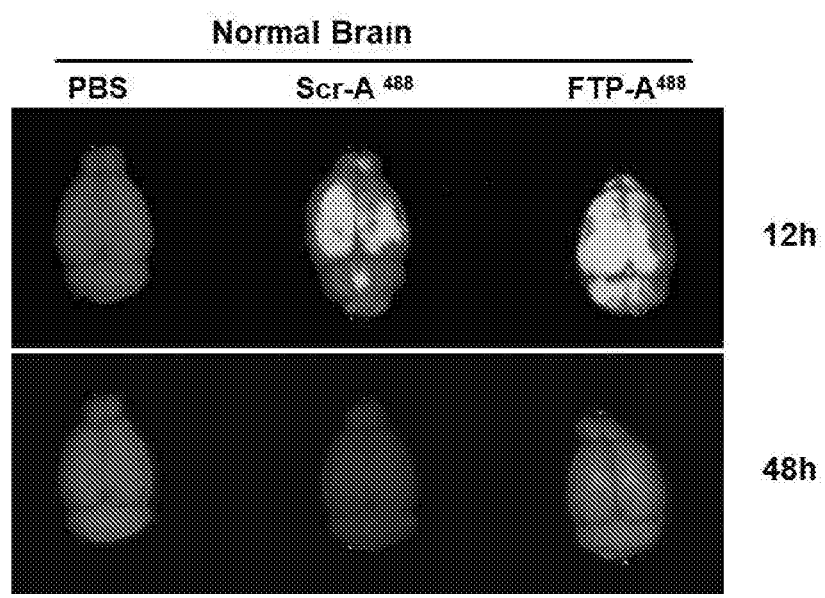
FIG. 5 illustrates the intracellular distribution of an intranasally inoculated Alexa$^{488}$ labeled FTP (FTP-A$^{488}$) in normal rats (three individuals per group), wherein the presence of fluorescence in the brain was examined 12 hours and 48 hours after intranasal administration; and PBS, a scrambled peptide labeled with Alexa$^{488}$ (Scr-A$^{488}$), and FTP labelled with Alexa$^{488}$ (FTP-A$^{488}$) were observed at indicated time point.
Figure 6:
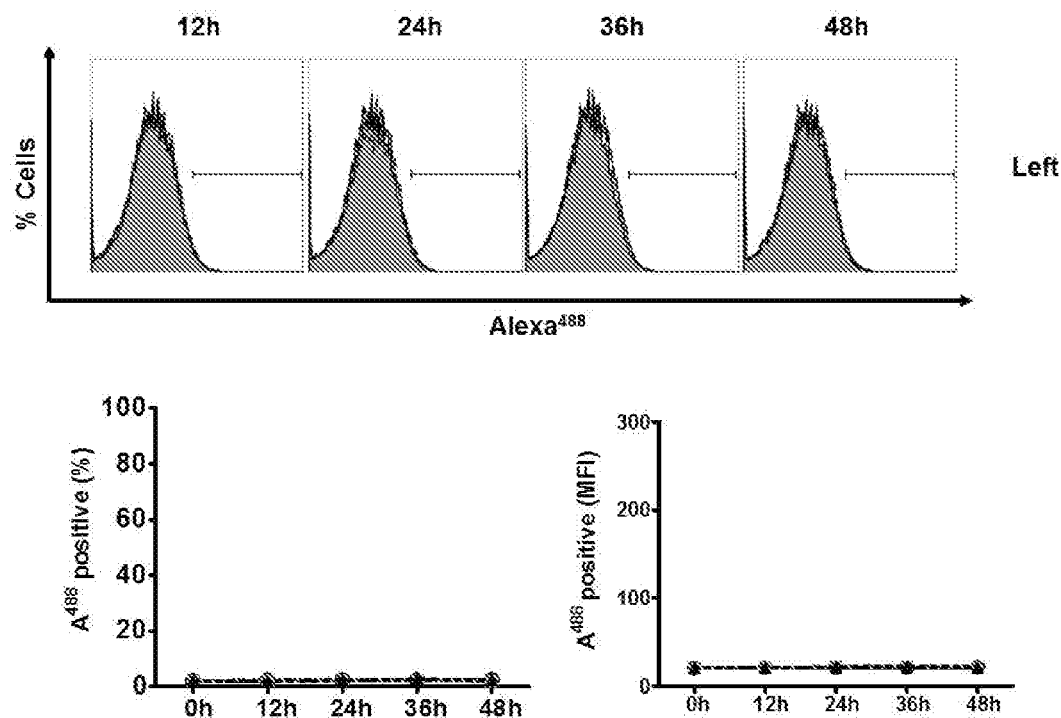
FIG. 6 illustrates flow cytometry analysis results of single cells obtained from the left hemisphere in rats intranasally inoculated with FTP-A$^{488}$ wherein a single cell suspension derived from the contralateral core of each representative group (n=3) was analyzed at indicated hour's post-inoculation of MCAO rats with PBS, Scr-A$^{488}$ FTP-A$^{488}$; and the drawing shows representative histograms (upper panel), cumulative data representing % FTP-Alexa$^{488}$-bound cells (lower left panel), and MFI (lower right panel); and the filled histograms correspond to PBS-treated rats, and the dotted and open histograms respectively represent Scr-FTP-bound cells and FTP-bound cells.

To target Fas in vivo, the FTP was directly delivered to the brain via a nasal route using a POD device developed by Impel Neuropharma[4]. As a result of intranasal inoculation of FTP-Alexa$^{488}$, the localization of labeled peptides occurred not only in MCAO-induced rats, but also in normal rats at 12 hours (see FIGS. 4C and 5). Interestingly, about 48 hours after the inoculation, FTP-A$^{488}$ was maintained in the brains of MCAO-treated rats and also in the ipsilateral brain regions thereof, suggesting that Fas expression indicates peptide affinity for the injured region. From the fact that the scrambled peptide (Scr-A$^{488}$) was not maintained in MCAO-induced rats 48 hours after the inoculation in spite of strong localization 12 hours thereafter, the specificity of FTP-Fas interaction was reinforced (see FIG. 4C). In addition, as a result of flow cytometry analysis of single cell suspensions derived from the ipsilateral brain region, FTP-A$^{488}$ was seen to bind to cells predominantly in the affected region of the right ischemic hemisphere with ~19%, 61%, and 73% of FTP positive cells 12, 24 and 48 hours after inoculation with the Scr-A$^{488}$ group or non-injured contralateral brain region in MCAO rats (see FIGS. 4D and 6).

Next, to measure whether FTP brain targeting was specific to the brain or other non-targeting organs were much more exposed, peripheral tissues for distribution were examined.

Figure 7:
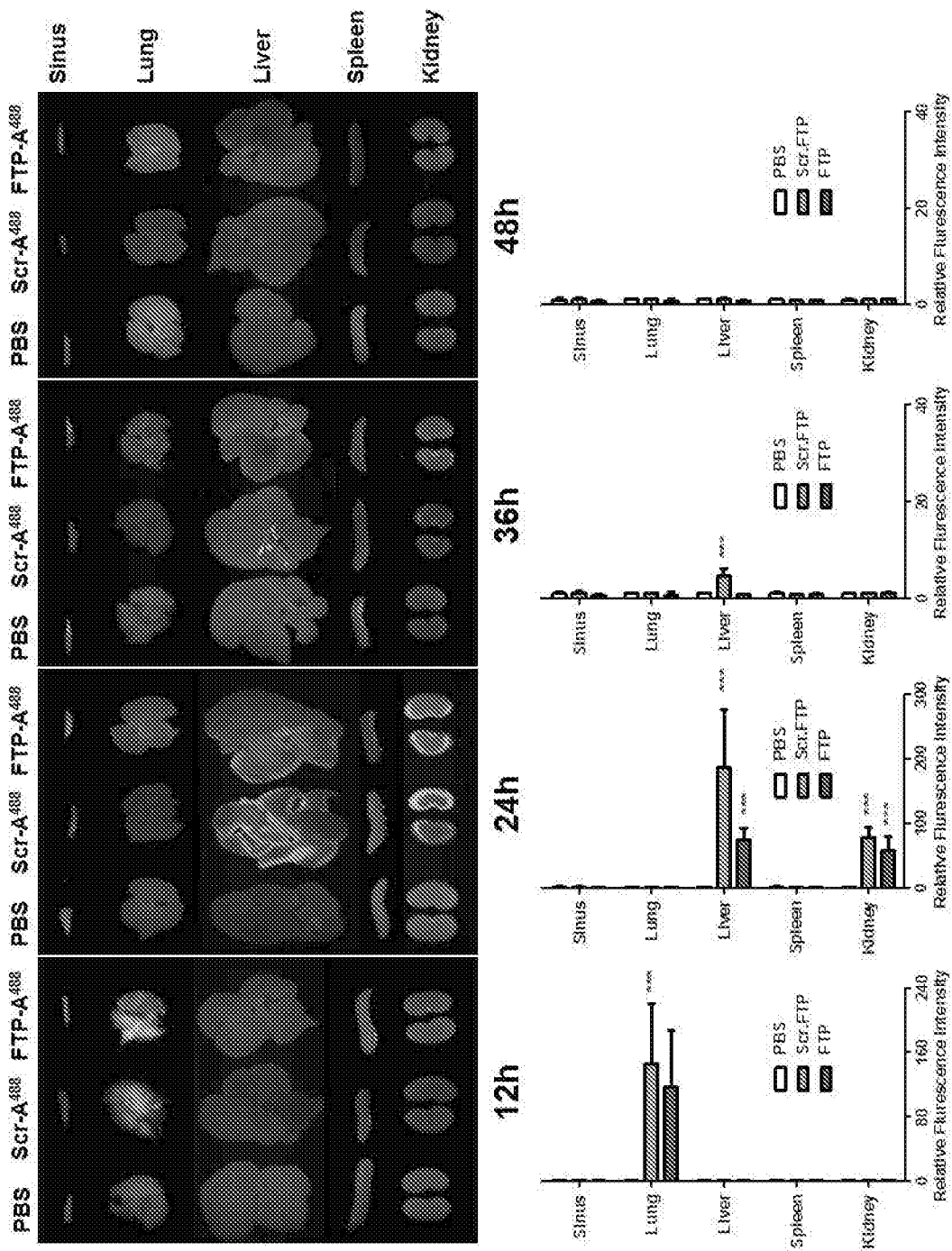
FIG. 7 illustrates the intracellular distribution of an intranasally inoculated Alexa$^{488}$ labeled FTP in a MCAO rat model (n=3) at indicated hour's post-inoculation, wherein a sinus, lung, liver, spleen, and kidney of rats inoculated with PBS, Scr-FTP-Alexa$^{488}$' or FTP-Alexa$^{488}$ were examined; and the drawing shows representative images of specific organs (upper panel) and cumulative data (lower panel) representing average fluorescence intensity measured at an arbitrary pixel value for each isolated organ from indicated test cohort±standard error, obtained from three rats.

As a result, a slight fluorescence signal was found in the lungs at the initial 12 hours after inoculation of both Scr-A$^{488}$ and FTP-A$^{488}$, whereas no signal was found in other organs, suggesting drainage of a limited peptide to the lung through the trachea (see FIG. 7). However, 24 hours after the inoculation, fluorescence exposure was seen much more in the liver and kidneys of the Scr-A$^{488}$ group than those of the FTP-A$^{488}$ group, which indicates systemic drainage of a non-targeting peptide from the brain to a peripheral gap (see FIG. 7). These results show that FTP retention in ischemic areas of the brains of MCAO rats is due to a combination of Fas expression in these areas.

Figure 4E:
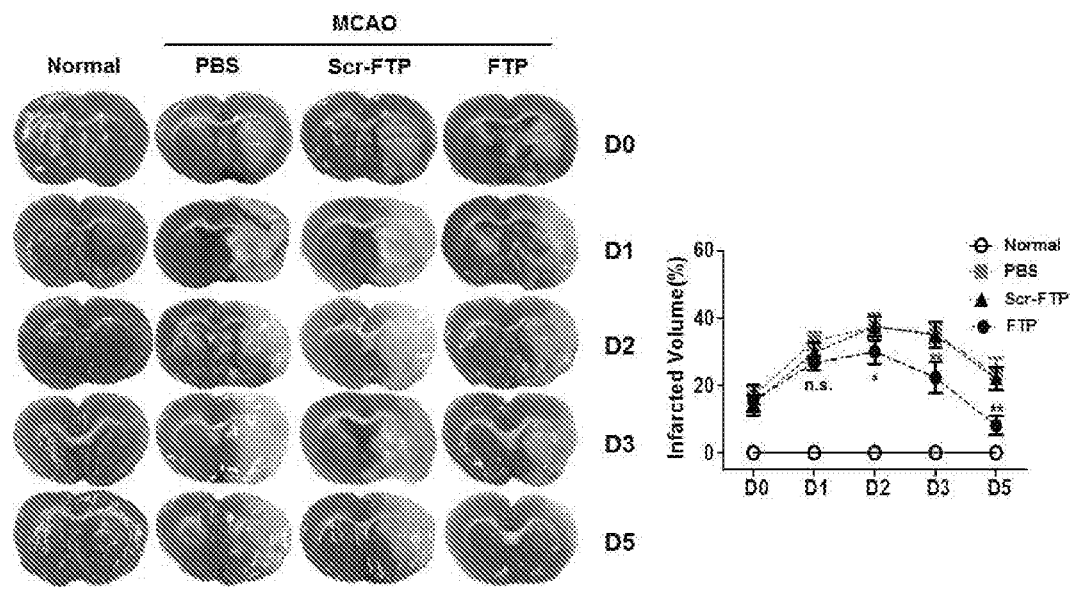
FIG. 4E illustrates measurement results of a cerebral infarction after FTP treatment, wherein representative 2,3,5-triphenyltetrazolium chloride (TTC) staining data shows a cerebral infarction (left) and the percentage (%) of infarcted volume (right) in each group (three individuals) at indicated days post-reperfusion.

Acute cerebral ischemia conditions in rat models cause prominent brain damage by regulating several apoptotic molecules[1]. The rats were stained with 2,3,5-TTC, followed by reperfusion every day, and then 1 hour-MCAO brain tissue slices were obtained from MCAO rats analyzed for 1 day to 5 days. As a result, significant infarct sizes were verified as soon as 12 hours (day 0, see FIG. 4E) after MCAO as evidenced by white TTC-negative areas. The infarct sizes predominantly increased in almost the entire right hemisphere until 24 hours (day 1) after MCAO, suggesting that 1 hour MCAO is sufficient to induce apoptosis. As expected, normal rat coronal brain sections and contralateral brain regions from MCAO animals did not show signs of infraction (see FIG. 4E, left panel).

Figure 4F:
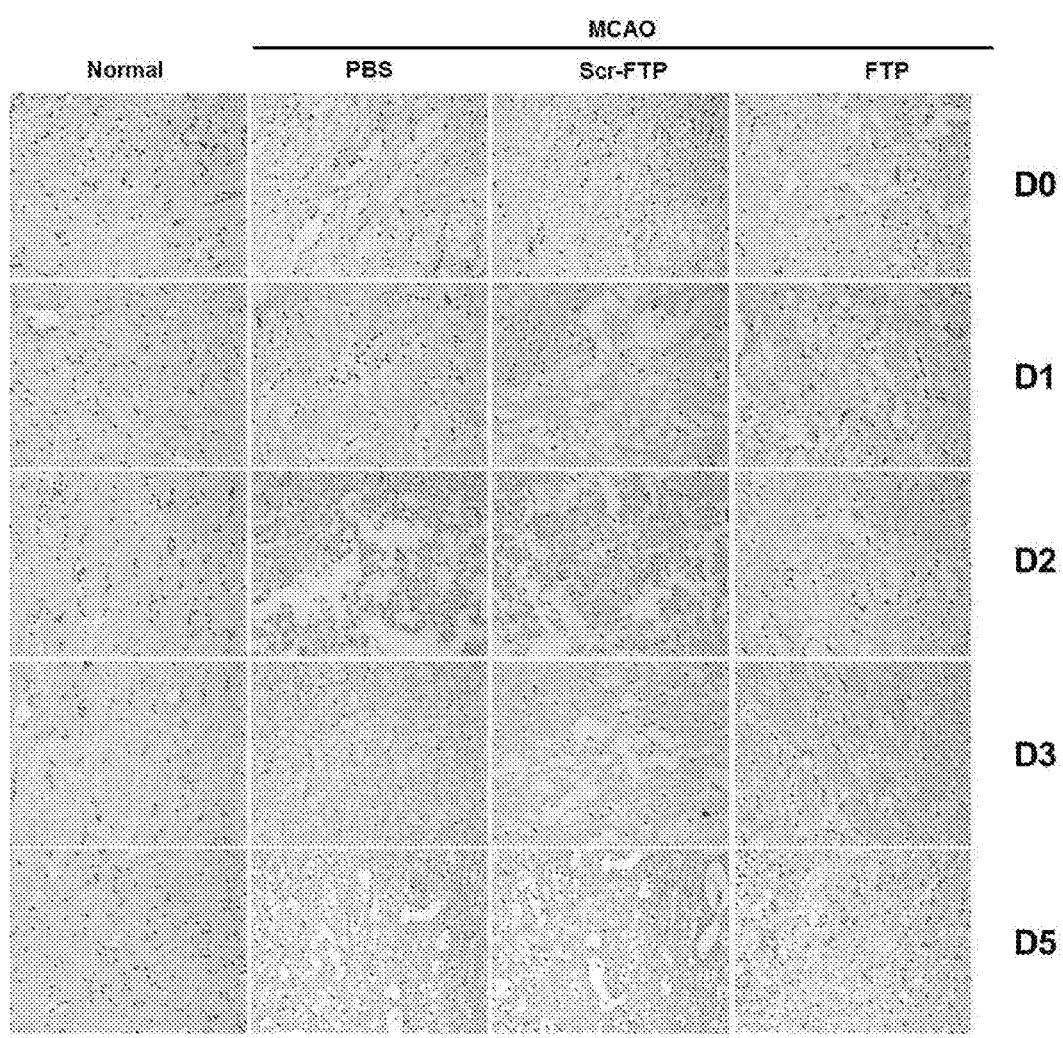
FIG. 4F illustrates representative hematoxylin and eosin (H&E) staining of the brain using H&E stained and paraffin-embedded sections obtained from normal or MCAO-subjected brains from PBS-Scr-FTP- or FTP-treated rats at indicated days post-reperfusion.
Figure 4G:
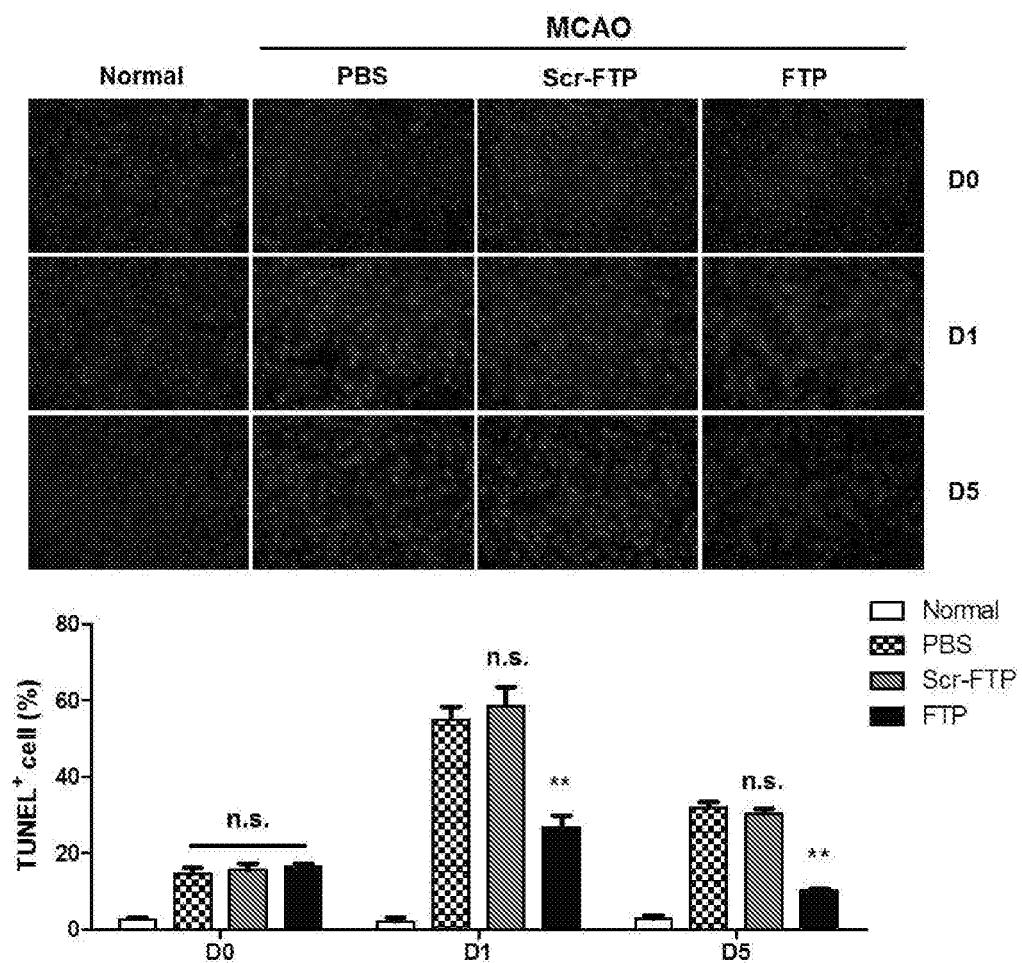
FIG. 4G illustrates terminal transferase-mediated dUTP nick end labeling (TUNEL) staining results of the brain, in which apoptosis in MCAO rats obtained from test rats was measured at indicated days post-reperfusion, wherein representative images of brain sections (g, upper panel) show TUNEL positive cells (red) and DAPI-stained nuclei (blue) in normal or ipsilateral cores of MCAO-induced rats inoculated with PBS, scr-FTP or a FTP; TUNEL positive cells are shown from rat groups (three individuals per group) (lower panel), and values are expressed as TUNEL positive cells±SD.

To evaluate the effect of FTP administration on brain infarction, individuals were administered 15 mmol I.N. 12 hours after reperfusion. Compared to Mock (PBS)- or Scr-FTP-treatment, the FTP significantly reduced the size of the infarcted area as early as day 1 after MCAO, and the individuals were almost completely recovered from the infract occurring on day 5 after reperfusion. In FTP-inoculated group, the infarct volume was observed to decrease to 26%, 29%, 18%, and 7% after day 1, day 2, day 3, and day 5, respectively. In a saline-treated group, although a severe cerebral infarct with a volume of 32% was found 24 hours after reperfusion, this infarct volume was increased to 37% and 35% on day 2 and day 3 and was 23% on day 5. As a result of immunohistochemical analysis, an increased intensity was seen on day 1 after reperfusion, and significant structural brain damage was seen in the right ischemic region of the brain as soon as 12 hours after reperfusion (see FIG. 4F). In contrast to TTC staining results, in the FTP-inoculated group, the interstitial edema and pyknotic nuclei started to reduce on day 1 after reperfusion and were alleviated on day 5 thereafter. The numbers of TUNEL positive cells were approximately 15% in all groups as soon as 12 hours after reperfusion, and increased to 54% and 32% in the PBS-inoculated group on day 1 and day 5, respectively, after reperfusion. The FTP treatment significantly decreased the number of apoptotic cells to 26% and 9% on day 1 and day 5, respectively, after reperfusion (see FIG. 4G). In addition, the absence of TUNEL positive cells in the contralateral region of MCAO brains indicates that apoptosis is specific to only an ischemic brain region (now shown).

Figure 4H:
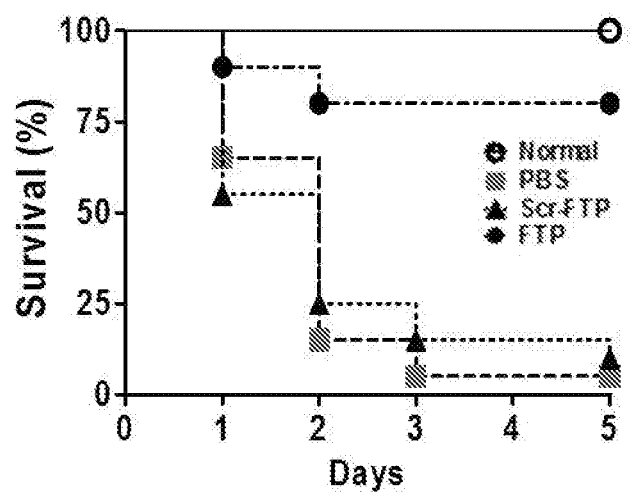
FIG. 4H illustrates Kaplan-Meier survival curves at indicated days post-reperfusion, wherein data was combined from each group (20 individuals), and % survival was calculated.
Figure 4I:
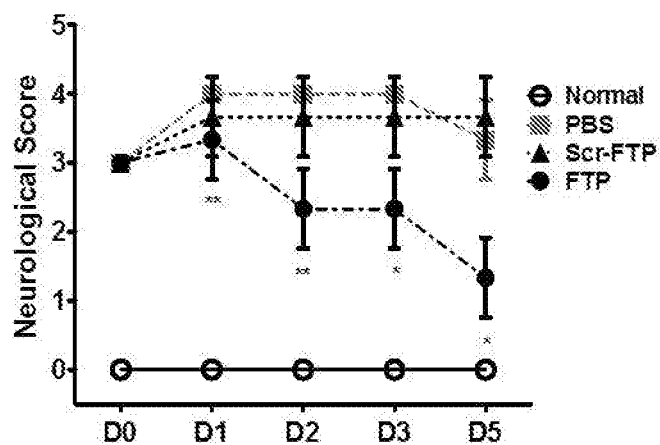
FIG. 4I illustrates neurological scores of tested rats, wherein neurological scores were calculated from each tested group (n=3) by measuring grades at indicated days; data is expressed as mean±SD of three independent experiments; and *$P<0.1$, $P<0.01$, *$P<0.001$, and n.s denotes not-significant.

Animals subjected to MCAO procedures have a high risk of dying within several days after surgery. Thus, in PBS-, Scr-FTP- and FTP-inoculated groups, changes in animal survival were observed. To examine the survival effect of FTP from day 1 until day 5 after reperfusion, the survival rate was calculated using a Kaplan-Meier method. Of the 18 rats per group, 12 rats in the saline-treated group, 11 rats in the Scr-FTP-treated group, and 2 rats in the FTP-treated group died over time (see FIG. 4H). As a result of evaluation, 65%, 15%, and 5% of the rats inoculated with PBS survived for 1 to 5 days after reperfusion. In the case of intranasal delivery of FTP, 90%, 80%, and 80% of the animals survived for 1 to 5 days compared to the PBS-treated group. Animals subjected to MCAO procedures exhibit abnormalities in terms of neuro-functional scales within a few hours after reperfusion. In the present example, a progressive effect on behavior was exhibited within 12 hours after MCAO, and the effect worsened between day 1 and day 5 in both the PBS and Scr-FTP inoculated groups. All the animals moved in a circle towards the paretic side when tails thereof were pulled, within 12 hours after reperfusion (grade 3), and spontaneous movement became severe between day 1 and day 3 after MCAO (grade 4) (see FIG. 4G). The neurological deficits score was improved in the FTP-treated group compared to the saline-treated group (see FIG. 4I). Neurological functions in the FTP-treated group were graded an average of 3.3, 2.3, 2.3, and 1.3 between day 1 and day 5 after reperfusion. In addition, these results demonstrate that the blocking apoptotic Fas signaling cascades by FTP not only reduces apoptosis, but also improves survival and neurological deficits in animals with cerebral ischemia.

The present invention may be used in the field for preventing or treating ischemic cerebrovascular diseases.

REFERENCES

1. Chelluboina, B., Klopfenstein, J. D., Gujrati, M., Rao, J. S. & Veeravalli, K. K. Temporal regulation of apoptotic and anti-apoptotic molecules after middle cerebral artery occlusion followed by reperfusion. *Molecular Neurobiology* 49, 50-65 (2014).
2. Yin, D. et al. Inhibition of apoptosis by hyperbaric oxygen in a rat focal cerebral ischemic model. *Journal of Cerebral Blood Flow & Metabolism* 23, 855-864 (2003).
3. Kumar, P. et al. Transvascular delivery of small interfering RNA to the central nervous system. *Nature* 448, 39-43 (2007).
4. Brown, V. & Liu, F. Intranasal delivery of a peptide with antidepressant-like effect. Neuropsychopharmacology 39, 2131-2141 (2014).

---

---

What is claimed is:

1. A method of treating an ischemic stroke, comprising intranasally administering a pharmaceutically effective amount of a pharmaceutical composition to a subject in need thereof, wherein the pharmaceutical composition comprises a linear FAS targeting peptide (FTP) having the amino acid sequence of SEQ ID NO: 1 and
   wherein the intranasal administration is performed while a subject is in a sleeping, anesthetized, or unconscious state.

2. The method of claim 1, wherein the pharmaceutical composition is contained in an injection device comprising a container configured to contain the pharmaceutical composition to be intranasally administered.

* * * * *

SEQUENCE LISTING

```
<160> NUMBER OF SEQ ID NOS: 2

<210> SEQ ID NO 1
<211> LENGTH: 8
<212> TYPE: PRT
<213> ORGANISM: Artificial Sequence
<220> FEATURE:
<223> OTHER INFORMATION: Synthetic

<400> SEQUENCE: 1

Tyr Cys Asp Glu His Phe Cys Tyr
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic

<400> SEQUENCE: 2

Tyr Cys Asn Ser Thr Val Cys Tyr
1               5
```